United States Patent
Nieuwoudt et al.

(10) Patent No.: US 6,375,807 B1
(45) Date of Patent: *Apr. 23, 2002

(54) SEPARATION OF ETHANOL MIXTURES BY EXTRACTIVE DISTILLATION

(76) Inventors: Izak Nieuwoudt, 12 Boschendal Avenue, Karindal Stellenbosch 7600; Braam Van Dyk, 2 Tertius Street, Amandaglen Durbanville 7550, both of (SA)

( * ) Notice: Subject to any disclaimer, the term of this patent is extended or adjusted under 35 U.S.C. 154(b) by 0 days.

This patent is subject to a terminal disclaimer.

(21) Appl. No.: 09/671,335

(22) Filed: Sep. 28, 2000

Related U.S. Application Data

(63) Continuation of application No. PCT/IB00/00074, filed on Jan. 26, 2000, and a continuation of application No. PCT/IB00/00076, filed on Jan. 26, 2000.

(30) Foreign Application Priority Data

| Jan. 28, 1999 | (SA) | 99/0641 |
| Jan. 28, 1999 | (SA) | 99/0643 |
| Jan. 28, 1999 | (SA) | 99/0644 |
| Jan. 28, 1999 | (SA) | 99/0645 |
| Jan. 28, 1999 | (SA) | 99/0660 |
| Jan. 28, 1999 | (SA) | 99/0661 |

(51) Int. Cl.[7] .......... B01D 3/40; C07C 27/32; C07C 29/84; C07C 67/54
(52) U.S. Cl. .......... 203/19; 203/57; 203/58; 203/59; 203/67; 203/68; 203/70; 568/913; 568/916; 560/248
(58) Field of Search .......... 203/59, 67, 58, 203/57, 68, 70, 19, 18; 568/913, 916; 560/248

(56) References Cited

U.S. PATENT DOCUMENTS

| 2,636,050 A | 4/1953 | Hoaglin et al. |
| 2,640,017 A | * 5/1953 | Graff .......... 203/18 |
| 4,379,028 A | 4/1983 | Berg et al. |
| 4,428,798 A | * 1/1984 | Zudkevitch et al. .......... 203/19 |
| 4,431,838 A | 2/1984 | Feldman et al. |
| 4,514,262 A | 4/1985 | Berg |
| 4,559,109 A | * 12/1985 | Lee et al. .......... 203/19 |
| 4,569,726 A | * 2/1986 | Berg et al. .......... 568/913 |
| 4,582,570 A | * 4/1986 | Mix .......... 568/916 |
| 4,584,063 A | 4/1986 | Berg et al. |
| 4,620,901 A | 11/1986 | Berg et al. |
| 5,085,739 A | * 2/1992 | Berg et al. .......... 568/916 |
| 5,145,562 A | 9/1992 | Brown et al. |
| 5,449,440 A | * 9/1995 | Roscalli et al. .......... 203/78 |
| 5,453,166 A | 9/1995 | Berg |
| 5,800,681 A | 9/1998 | Berg |
| 5,897,750 A | 4/1999 | Berg |
| 5,993,610 A | * 11/1999 | Berg .......... 203/70 |

FOREIGN PATENT DOCUMENTS

| EP | 0 047 204 A2 | 3/1982 |
| EP | 0047204 | * 5/1982 |
| EP | 0 496 060 A2 | 7/1992 |
| GB | 877 360 | 9/1961 |
| JP | 54 119 411 | 9/1979 |

OTHER PUBLICATIONS

Cepeda E et al: "Separacion pro destilacion extractiva de mezclas formadas por alcoholes y sus esteres del acido acetico", An. Quim., Ser. A (AQSTDQ, 02111330); 1984; vol. 80 (3, Suppl. 2); pp. 755–759, XP000908880; Col. Univ. Alava; Dep. Quim. Tecn.; Vitoria; Spain (ES) (See English summary on p. 755).

* cited by examiner

*Primary Examiner*—Virginia Manoharan
(74) *Attorney, Agent, or Firm*—Larson & Taylor PLC

(57) ABSTRACT

A method of separating ethanol and ethyl acetate, and ethanol and water involves distilling a mixture of the components by an extractive distillation process in the presence of an extractive distillation solvent. The extractive distillation solvent may be an amine, an alkylated thiopene, and paraffins.

5 Claims, 1 Drawing Sheet

SEPARATION OF ETHANOL MIXTURES BY EXTRACTIVE DISTILLATION

This is a continuation of International PCT Application Numbers PCT/IB00/00074 and PCT/IB00/00076, filed on Jan. 26, 2000.

Extractive distillation is a process to separate close-boiling compounds from each other by introducing a selectively-acting third component, the extractive distillation solvent, with the result that the relative volatility of the mixture to be separated is increased and azeotropes, if present, are overcome. The extractive distillation solvent Is to be selected such that it does not form an undesired azeotrope with any of the compounds in the mixture. The invention suggests a method of separation of ethanol and ethyl acetate, and ethanol and water by distilling a mixture of the components by way of an extractive distillation process in the presence of an extractive distillation solvent.

Separation of components from ethanol mixtures thereof by extractive distillation.

FIELD OF INVENTION

The present invention relates to the separation of components from ethanol mixtures thereof by extractive distillation.

BACKGROUND TO INVENTION

Extractive distillation is a process to separate close-boiling compounds from each other by introducing a selectively-acting third component, the extractive distillation solvent, with the result that the relative volatility of the mixture to be separated is increased and azeotropes, if present, are overcome. The extractive distillation solvent is to be selected such that it does not form an undesired azeotrope with any of the compounds in the mixture.

The separation of ethanol and ethyl acetate is complicated due to the existence of an azeotrope. Trimethylbenzene has been proposed in the literature as extractive distillation solvents to produce ethanol as distillate.

The separation of ethanol and water is complicated due to the existence of an azeotrope. Azeotropic distillation using benzene or cyclohexane is commonly used to effect the separation. Membrane separation, such as pervaporation, may alternatively be used to break the azeotrope. Pressure swing distillation is another separation method that may be used to produce pure ethanol and pure water. All of these methods utilize two distillation columns. In the case of azeotropic distillation, a phase separation device is needed. In the case of membrane separation, membrane modules are needed. Extractive distillation can also be used to effect the desired separation. This method also uses a two column system but the operation is simple. Ethylene glycol has been proposed in the literature as an extractive distillation solvent for the system ethanol/water.

As has been stated in U.S. Pat. No. 5,800,681 (Berg) extractive distillation is the method of separating close boiling compounds from each other by carrying out the distillation in a multiplate rectification column in the presence of an added liquid or liquid mixture, said liquid(s) having a boiling point higher than the compounds being separated. The extractive distillation solvent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive distillation solvent should boil higher than any of the close boiling liquids being separated and not form minimum azeotropes with them. Usually the extractive distillation solvent is Introduced a few plates from the top of the column to ensure that none of the extractive distillation solvent is carried over with the lowest boiling component.

It is an object of this invention to suggest at least one further extractive distillation solvent for the separation of components from ethanol mixtures thereof.

SUMMARY OF INVENTION

According to the invention, a method of separation of ethanol from a mixture of ethanol and another compound selected from a first group consisting of ethyl acetate and water, includes the step of distilling the mixture containing at least ethanol and another compound selected from a first group consisting of ethyl acetate and water by way of an extractive distillation process in the presence of an extractive distillation solvent selected from a second group consisting of an amine, an alkylated thiopene, a paraffin and a chlorinated carbon.

The mixture may contain ethanol and ethyl acetate and the extractive distillation solvent may be selected from the group consisting of an amine, an alkylated thiopene and a paraffin.

The ethanol and ethyl acetate mixture may contain only ethanol and ethyl acetate.

The amine may be selected from a group consisting of N,N'-dimethyl-1, 3-propanediamine, N-N'-dimethylethylenediamine, diethylene triamine, hexamethylene diamine and 1,3-diaminopentane.

The alkylated thiopene may be ethyl thiopene.

The paraffin may be at least one of the components selected from the group consisting of dodecane, tridecane and tetradecane.

The mixture may contain ethanol and water and the extractive distillation solvent may be selected from the group consisting of an amine and a chlorinated hydrocarbon.

The ethanol and water mixture may contain only ethanol and water.

The amine may be selected from a group consisting of diaminobutane, 1,3-diaminopentane and diethylene triamine.

The chlorinated hydrocarbon may be hexachlorobutadiene.

BRIEF DESCRIPTION OF DRAWING

The invention will now be described by way of example with reference to the accompanying schematic drawing.

In the drawing there is shown a schematic view of an experimental apparatus for testing an extractive distillation solvent for separating components from mixtures thereof in accordance with the invention.

DETAILED DESCRIPTION OF THE PREFERRED EMBODIMENTS

Figure 1:
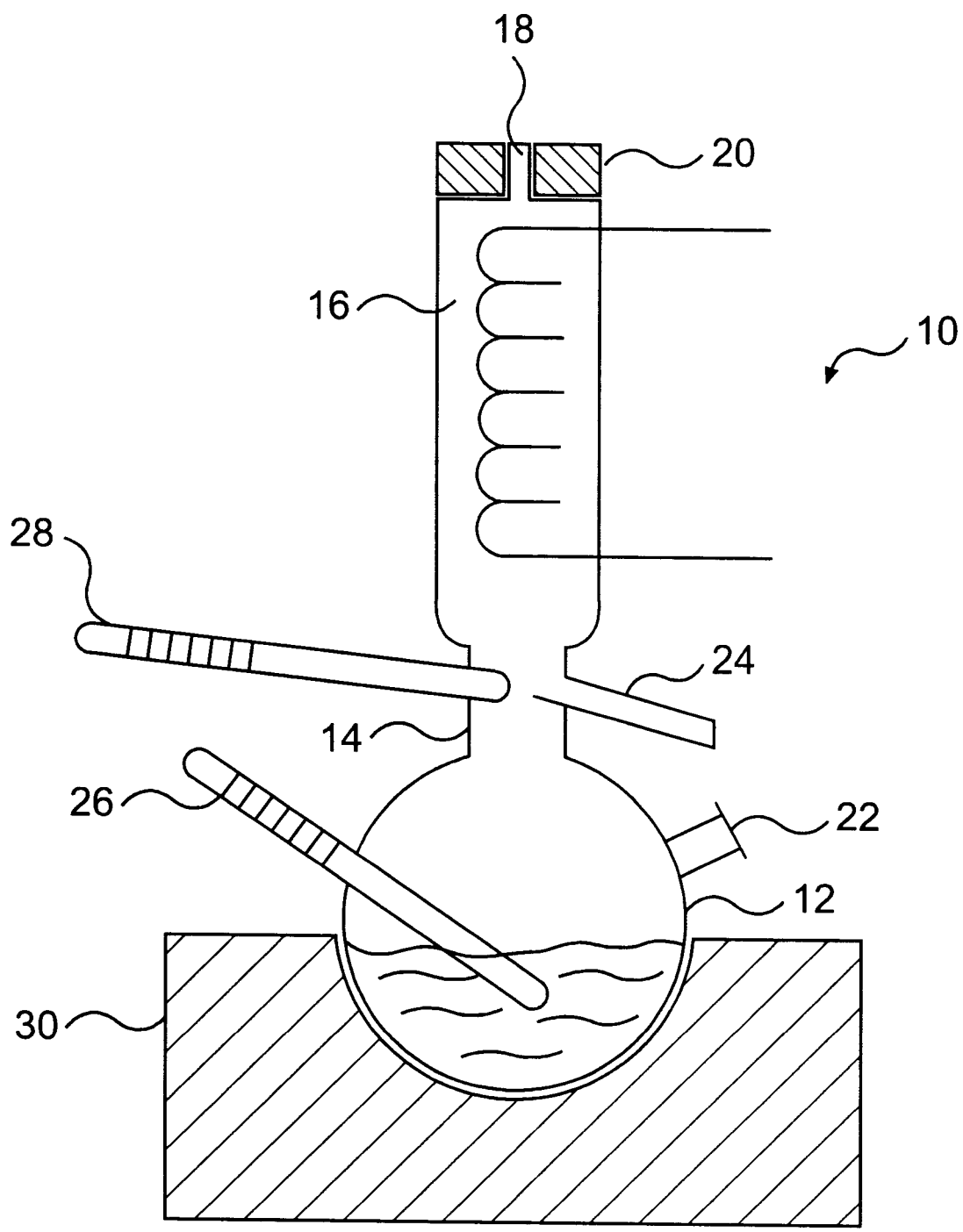

In the drawing there is shown a vapour-liquid equilibrium still 10 Including a bulb flask 12 having a tube 14 leading to a condenser 16 and terminating in an outlet 18. The outlet 18 has an electromagnetic closure mechanism 20.

A liquid phase sample conduit 22 leads into the flask 12.

A further liquid phase sample conduit 24 leads into the tube 14.

A first thermometer 26 is adapted to read the temperature of the liquid contained in the flask 12, and a second thermometer 28 is adapted to read the temperature of the vapour in the tube 14.

The flask 12 can be heated by a heating mantle 30.

The extractive distillation procedure is as follows:

A liquid mixture is prepared consisting of the components to be separated and, an extractive distillation solvent. The liquid is introduced into the bulb flask 12 via conduit 22.

The mixture in the bulb flask 12 is then heated by the heating mantle 30 and kept at boiling point.

During boiling the mixture separates into a liquid phase remaining in the bulb flask 12 and a vapour phase in the tube 14. In the tube 14 the vapour phase is cooled by the condenser 16, whereafter it condenses and returns as liquid to the bulb flask 12.

The mixture is boiled and condensed for several hours, normally 5 to 6 hours. The process of evaporation and condensation is repeated until equilibrium is reached between the vapour and liquid phases. Thereafter, a liquid sample of the liquid phase in the bulb flask 12 is extracted through conduit 22 and a liquid sample of the condensed vapour phase in the tube 14 Is extracted through conduit 24.

The temperature of the liquid phase in the bulb flask 12 is continuously monitored by the thermometer 26, and the temperature of the vapour phase in the tube 14 is continuously monitored by the thermometer 28.

Experiment 1

An ethanol/ethyl acetate mixture with a molar ratio of 1:1 has a relative volatility of 0.92.

The separation was effected by using a suitable amine as an extractive distillation solvent.

A mixture of ethanol (16.8 g), ethyl acetate (31.2 g) and di-ethylene-triamine (289.8 g) was charged into the flask 12 of the vapour-liquid equilibrium still 10 and the above procedure was applied. The liquid and vapour phases were analysed. The liquid and vapour molar fractions were determined to be as follows:

TABLE 1

| Component | Liquid (mole fraction) | Vapour (mole fraction) |
|---|---|---|
| Ethanol | 0.103 | 0.725 |
| Ethyl Acetate | 0.100 | 0.275 |
| Di-ethylene-triamine | 0.797 | 0.000 |

This translates to a relative volatility of 2.56 for the system ethanol/ethyl acetate in the ternary system shown above, the ethanol being the distillate.

Experiment 2

An ethanol/ethyl acetate mixture with a molar ratio of 0.7:1 has a relative volatility of 1.05.

The separation was effected by using a suitable substituted thiophene as an extractive distillation solvent. A mixture of ethanol (2.3 g), ethyl acetate (6.0 g) and ethyl thiophene (24.7 g) was charged into the flask 12 of the vapour-liquid equilibrium 10 and the above procedure was applied. The liquid and vapour phases were analysed. The liquid and vapour molar fractions were determined to be as follows:

TABLE 2

| Component | Liquid (mole fraction) | Vapour (mole fraction) |
|---|---|---|
| Ethanol | 0.148 | 0.690 |
| Ethyl Acetate | 0.202 | 0.295 |
| Ethyl Thiophene | 0.651 | 0.015 |

This translates to a relative volatility of 3.19 for the system ethanol/ethyl acetate in the ternary system shown above, the ethanol being the distillate.

Experiment 3

An ethanol/ethyl acetate mixture with a molar ratio of 1:1 has a relative volatility of 0.91.

The separation was effected by using a suitable paraffin as an extractive is distillation solvent. A mixture of ethanol (9.7 g), ethyl acetate (17.7 g) and dodecane (238.2 g) was charged into the flask 12 of the vapour-liquid equilibrium still 10 and the above procedure was applied. The liquid and vapour phases were analysed. The liquid and vapour molar fractions were determined to be as follows:

TABLE 3

| Component | Liquid (mole fraction) | Vapour (mole fraction) |
|---|---|---|
| Ethanol | 0.116 | 0.707 |
| Ethyl Acetate | 0.111 | 0.280 |
| Dodecane | 0.773 | 0.013 |

This translates to a relative volatility of 2.41 for the system ethanol/ethyl acetate in the ternary system shown above, the ethanol being the distillate.

An ethanol/water liquid mixture with a molar ratio of 1.25:1 has a relative volatility of 1.71.

The separation was effected by using a suitable amine as an extractive distillation solvent.

A mixture of ethanol (23.7 g), water (7.4 g) and diethylenetriamine (330.7 g) was charged into the flask 12 of the vapour-liquid equilibrium still 10 and the above procedure was applied. The liquid and vapour phases were analysed. The liquid and vapour molar fractions were determined to be as follows:

TABLE 4

| Component | Liquid (mole fraction) | Vapour (mole fraction) |
|---|---|---|
| Ethanol | 0.125 | 0.750 |
| Water | 0.100 | 0.250 |
| Diethylenetriamine | 0.776 | 0.000 |

This translates to a relative volatility of 2.4 for the system ethanol/water in the ternary system shown above, the ethanol being the distillate.

Experiment 5

An ethanol/water liquid mixture with a molar ratio of 4:1 has a relative volatility of 1.12.

The separation was effected by using a suitable amine as an extractive distillation solvent.

A mixture of ethanol (11.1 g), water (1.1 g) and 1,3-diaminopentane (197.7 g) was charged into the flask 12 of the vapour-liquid equilibrium still 10 and the above procedure was applied. The liquid and vapour phases were analysed. The liquid and vapour molar fractions were determined to be as follows:

TABLE 5

| Component | Liquid (mole fraction) | Vapour (mole fraction) |
| --- | --- | --- |
| Ethanol | 0.108 | 0.732 |
| Water | 0.027 | 0.242 |
| 1,3-diaminopentane | 0.865 | 0.026 |

This translates to a relative volatility of 1.33 for the system water/ethanol in the ternary system shown above, the water being the distillate.

Experiment 6

An ethanol/water mixture with a molar ratio of 0.9:1 has a relative volatility of 2.07.

The separation was effected by using a suitable chlorinated hydrocarbon as an extractive distillation solvent.

A mixture of ethanol (16.34 g), water (7.1 g) and hexachlorobutadiene (372.2 g) was charged into the flask 12 of the vapour-liquid equilibrium still 10 and the above procedure was applied. The liquid and vapour phases were analysed. The liquid and vapour molar fractions were determined to be as follows:

TABLE 6

| Component | Liquid (mole fraction) | Vapour (mole fraction) |
| --- | --- | --- |
| Ethanol | 0.163 | 0.682 |

TABLE 6-continued

| Component | Liquid (mole fraction) | Vapour (mole fraction) |
| --- | --- | --- |
| Water | 0.181 | 0.311 |
| Hexachlorobutadiene | 0.656 | 0.007 |

This translates to a relative volatility of 2.43 for the system ethanol/water in the ternary system shown above, the ethanol being the distillate.

What is claimed is:

1. A method of separation of ethanol and ethyl acetate, comprising distilling a mixture of ethanol and ethyl acetate containing at least ethanol and ethyl acetate by an extractive distillation process in the presence of an extractive distillation solvent selected from the group consisting of an amine selected from the group consisting of N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and a chlorinated paraffin.

2. The method as claimed in claim 1, wherein the ethanol and ethyl acetate mixture contains only ethanol and ethyl acetate.

3. The method as claimed in claim 1, wherein the alkylated thiopene comprises ethyl thiopene.

4. A method of separation of ethanol and water, comprising distilling a mixture of ethanol and water containing at least ethanol and water by an extractive distillation process in the presence of an extractive distillation solvent selected from the group consisting of diaminobutane, 1,3-diaminopentane, diethylenetriamine, and hexachlorobutadiene.

5. The method as claimed in claim 4, wherein the ethanol and water mixture contains only ethanol and water.

* * * * *